(12) United States Patent
Kinser

(10) Patent No.: US 11,045,141 B2
(45) Date of Patent: Jun. 29, 2021

(54) BIOSENSOR CALIBRATION STRUCTURE CONTAINING DIFFERENT SENSING SURFACE AREA

(71) Applicant: International Business Machines Corporation, Armonk, NY (US)

(72) Inventor: Emily R. Kinser, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/685,579

(22) Filed: Nov. 15, 2019

(65) Prior Publication Data

US 2020/0077956 A1    Mar. 12, 2020

Related U.S. Application Data

(63) Continuation of application No. 15/446,782, filed on Mar. 1, 2017, now Pat. No. 10,548,530.

(51) Int. Cl.
| | |
|---|---|
| *A61B 5/145* | (2006.01) |
| *A61B 5/1486* | (2006.01) |
| *G01N 33/543* | (2006.01) |
| *A61B 5/00* | (2006.01) |

(52) U.S. Cl.
CPC ........ *A61B 5/6846* (2013.01); *A61B 5/14532* (2013.01); *A61B 5/14865* (2013.01); *G01N 33/5438* (2013.01); *A61B 5/14546* (2013.01); *A61B 2560/0223* (2013.01); *A61B 2562/0295* (2013.01); *A61B 2562/125* (2013.01)

(58) Field of Classification Search
None
See application file for complete search history.

(56) References Cited

U.S. PATENT DOCUMENTS

| | | | |
|---|---|---|---|
| 2,933,458 | A | 4/1960 | King et al. |
| 6,136,630 | A | 10/2000 | Weigold et al. |
| 6,359,444 | B1 | 3/2002 | Grimes |
| D469,540 | S | 1/2003 | Holker et al. |

(Continued)

FOREIGN PATENT DOCUMENTS

| | | |
|---|---|---|
| CN | 1598694 A | 3/2005 |
| CN | 106094426 A | 11/2016 |
| KR | 1020160092635 A | 8/2016 |

OTHER PUBLICATIONS

Office Action dated Jul. 23, 2020 received in U.S. Appl. No. 16/169,654.
Office Action dated Jun. 9, 2020 received in U.S. Appl. No. 16/245,942.
List of IBM Patents or Patent Applications Treated as Related, dated Jul. 2, 2020, 2 pages.

(Continued)

*Primary Examiner* — J. Christopher Ball
(74) *Attorney, Agent, or Firm* — Scully, Scott, Murphy & Presser, P.C.; Steven J. Meyers

(57) ABSTRACT

A biosensor calibration structure is provided that includes at least two electrode structures in which at least one of the electrode structures has a non-random nanopattern on the sensing surface which provides a different sensing surface area than at least one other electrode structure. The at least one other electrode structure may be non-patterned (i.e., flat) or have another non-random nanopattern on the sensing surface. A biological functionalization material such as, for example, glucose oxidase or glucose dehydrogenase, can be located on at least the sensing surface of each electrode structure. The biosensor calibration structure can be used within a biosensor calibration method.

10 Claims, 3 Drawing Sheets

(56) References Cited

U.S. PATENT DOCUMENTS

| | | |
|---|---|---|
| 6,914,279 B2 | 7/2005 | Lu et al. |
| 7,005,048 B1 | 2/2006 | Watanabe et al. |
| 7,294,910 B2 | 11/2007 | Thomas et al. |
| 7,524,408 B2 | 4/2009 | Monbouquette et al. |
| 7,604,592 B2 | 10/2009 | Freeman et al. |
| 7,627,938 B2 | 12/2009 | Kim et al. |
| 7,894,914 B2 | 2/2011 | Stahmann et al. |
| 7,949,382 B2 | 5/2011 | Jina |
| 7,955,483 B2 | 6/2011 | Gu et al. |
| 8,076,125 B2 | 12/2011 | McGimpsey |
| 8,097,926 B2 | 1/2012 | De Graff et al. |
| 8,221,822 B2 | 7/2012 | Flanagan et al. |
| 8,303,800 B2 | 11/2012 | Fukuda et al. |
| 8,485,245 B1 | 7/2013 | Prest et al. |
| 8,529,835 B2 | 9/2013 | Kaplan et al. |
| 8,668,978 B2 | 3/2014 | Malima et al. |
| 8,741,380 B2 | 6/2014 | Yoshida et al. |
| 8,772,228 B2 | 7/2014 | Stupp et al. |
| 8,808,516 B2 | 8/2014 | Melosh et al. |
| 8,907,384 B2 | 12/2014 | Pace et al. |
| 9,958,441 B2 | 5/2018 | Zhang et al. |
| 2005/0269285 A1 | 12/2005 | Jung et al. |
| 2007/0148653 A1 | 6/2007 | Yoshida |
| 2009/0137423 A1 | 5/2009 | Higson |
| 2009/0155800 A1 | 6/2009 | Hong et al. |
| 2009/0243584 A1 | 10/2009 | Zhang et al. |
| 2009/0272285 A1 | 11/2009 | Kraus et al. |
| 2010/0006451 A1 | 1/2010 | Gordon et al. |
| 2010/0066346 A1 | 3/2010 | Zhang et al. |
| 2010/0310773 A1 | 12/2010 | Yoshida et al. |
| 2010/0318193 A1 | 12/2010 | Desai et al. |
| 2011/0027458 A1 | 2/2011 | Boock et al. |
| 2011/0073475 A1 | 3/2011 | Kastanos et al. |
| 2011/0091510 A1 | 4/2011 | Lele et al. |
| 2011/0230735 A1 | 9/2011 | Wolfe et al. |
| 2011/0233063 A1 | 9/2011 | Seki et al. |
| 2011/0301716 A1 | 12/2011 | Sirivisoot et al. |
| 2011/0319734 A1 | 12/2011 | Gottlieb et al. |
| 2012/0218550 A1 | 8/2012 | O'Mahony |
| 2012/0312061 A1 | 12/2012 | Pham et al. |
| 2013/0025814 A1 | 1/2013 | Demetriou et al. |
| 2013/0079608 A1 | 3/2013 | Miller et al. |
| 2013/0112321 A1 | 5/2013 | Poole et al. |
| 2013/0150822 A1 | 6/2013 | Ross |
| 2014/0230854 A1 | 8/2014 | Lopez et al. |
| 2014/0238574 A1 | 8/2014 | Kinser |
| 2016/0331290 A1 | 11/2016 | Oh et al. |
| 2017/0025453 A1 | 1/2017 | Bornfreund et al. |
| 2017/0202079 A1 | 7/2017 | Norton et al. |
| 2017/0209079 A1 | 7/2017 | Kinser et al. |
| 2017/0241003 A1 | 8/2017 | Na et al. |
| 2018/0020957 A1 | 1/2018 | Kinser |
| 2018/0217080 A1 | 8/2018 | Kinser |
| 2018/0252662 A1 | 9/2018 | Kinser |
| 2019/0056343 A1 | 2/2019 | Kinser |
| 2019/0142310 A1 | 5/2019 | Kinser et al. |
| 2020/0077956 A1 | 3/2020 | Kinser |

OTHER PUBLICATIONS

Padmanabhan, J., et al., "Engineering Cellular Response Using Nanopatterned Bulk Metallic Glass", American Chemical Society Nano, Apr. 2014, pp. 4366-4375, vol. 8, No. 5.

Zhai, D. et al., "Highly Sensitive Glucose Sensor Based on Pt Nanoparticle/Polyaniline Hydrogel Heterostructures", ACS Nano, Mar. 2013, pp. 3540-3546, vol. 7, No. 4.

S.-H. Parng, et al. "Effect of temperature and glucose concentration on a glass-based sensor for long-term stability Investigation", J. Micro/Nanolith. MEMS MOEMS, Jan.-Mar. 2011, pp. 013003-1 to 013003-5, vol. 10(1).

J. Gajdzik, et al., "Enzyme immobilisation on self-organised nanopatterned electrode surfaces", Phys. Chem. Chem. Phys., Sep. 2010, pp. 12604-12607, 12.

M. Cardosi, et al., "Amperometric Glucose Sensors for Whole Blood Measurement Based on Dehydrogenase Enzymes", Intech, Dehydrogenases, Chapter 13, Published: Nov. 14, 2012, pp. 319-354.

D. C. Deshpande, et al., "Development of a nanoscale heterostructured glucose sensor using modified microfabrication processes", J. Micro/Nanolith, Apr.-Jun. 2008, MEMS MOEMS, pp. 023005-1 to 023005-6, vol. 7(2).

Freckmann, G., et al.,"System Accuracy Evaluation of 27 Blood Glucose Monitoring Systems According to DIN EN ISO 15197", Diabetes Technology & Therapeutics. Mar. 2010, pp. 221-231, vol. 12, No. 3.

Browne, D. J., et al., "Comparison of nucleation and growth mechanisms in alloy solidification to those in metallic glass crystallisation—relevance to modeling", Transactions of the Indian Institute of Metals, Aug.-Oct. 2009, pp. 109-412, vol. 62, Issues 4-5.

Pitt, E. B., et al., "Temperature dependence of the thermoplastic formability in bulk metallic glasses", Journal of Applied Physics, published online Aug. 23, 2011, 110, pp. 043518-1 to 043518-7.

List of IBM Patents or Patent Applications Treated as Related dated Nov. 15, 2019, 2 pages.

Mailoa, J. P., et al., "Textured Conducting Glass by Nanosphere Lithography for Increased Light Absorption in Thin-Film Solar Cells", J. Phys. D. Appl. Phys., Feb. 2014, 6 pages, vol. 47, No. 8, 058105.

Lee, S. H., et al., "Nanostructured indium-tin-oxide films fabricated by all-solution processing for functional transparent electrodes", Optics Express, Oct. 2011, pp. 21803-21808, Col. 19, No. 22.

Kaushik, N., et al., "Metallic glass thin films for potential biomedical applications," Journal of Biomedical Materials Research B: Applied Biomaterials, Oct. 2014, pp. 1544-1552, vol. 102B, Issue 7.

International Search Report dated May 14, 2018 received in a related foreign application.

Carmo, M., et al., "Bulk Metallic Glass Nanowire Architecture for Electrochemical Applications", American Chemical Society, Published online Mar. 3, 2011, pp. 2979-2983, vol. 5, No. 4.

Crystallography365, "GOLD! The crystal structure of success", posted on Jan. 17, 2014, 4 pages.

Office Action dated Apr. 6, 2018 received in parent U.S. Appl. No. 15/005,690.

BIOSENSOR CALIBRATION STRUCTURE CONTAINING DIFFERENT SENSING SURFACE AREA

BACKGROUND

The present application relates to biosensors for use in medical and environmental monitoring. More particularly, the present application relates to a biosensor calibration structure that includes at least two electrode structures in which at least one of the electrode structures has a non-random nanopattern on the sensing surface which provides a different sensing surface area than at least one other electrode structure. The present application also relates to a calibration method that employs the biosensor calibration structure of the present application.

Biosensors with enhanced signal and sensitivity are essential to provide reliable data for both medical and environmental monitoring. Such biosensors are especially needed for areas related to food and water supply security as well as the healthcare industry. For healthcare, glucose sensors comprise a significant portion of the existing biosensor market. Platinum (Pt) is commonly used as a working electrode in glucose sensors, and platinum has demonstrated biocompatibility. External electrochemical sensors (so-called "Test-Strips") are commonly used. However, limitations exist on the accuracy and applicability of test strip sensors.

In vivo glucose sensors, which are implanted into a human body, can be used to continuously monitor blood sugar. However, the foreign body response restricts the functionality of in vivo biosensors. Moreover, the foreign body response can reduce the sensor signal output over time. In some applications, the foreign body response may even reject the biosensor from the human body.

For biosensors used in vivo or in other environments in which sensor stability could be at risk, effective methods of real-time sensor calibration are essential to provide reliable sensor outputs that can be trusted for decision making. For example, as in vivo sensor signal degrades to encapsulation as part of the foreign body response, validating the calibration accuracy becomes more of a challenge. In order to improve sensor calibration accuracy, commercial manufactures of in vivo glucose sensors are shifting their calibration strategies to use multiple electrodes of a same material or a different material as a means for calibration. Although such techniques improve, to some degree, the sensor accuracy and useful lifetime, the formation of multiple electrodes (specifically of different materials) is time consuming and increases the cost associated with the production process. There is thus a need to provide a structure that can be used in biosensor calibration that has enhanced accuracy, increased useful lifetime, and is cost efficient to manufacture.

SUMMARY

A biosensor calibration structure is provided that includes at least two electrode structures in which at least one of the electrode structures has a non-random nanopattern on the sensing surface which provides a different sensing surface area than at least one other electrode structure. The at least one other electrode structure may be non-patterned (i.e., flat) or have another non-random nanopattern on the sensing surface. In some embodiments, a biological functionalization material such as, for example, glucose oxidase or glucose dehydrogenase, can be located on at least the sensing surface of each electrode structure. The biosensor calibration structure of the present application enables a hardware-based calibration method that maintains and, in some instances, enhances, sensor signal throughout the lifetime of the structure.

In one aspect of the present application, a biosensor calibration structure is provided. In one embodiment of the present application, the biosensor calibration structure may include an array of electrode structures each having a sensing surface, wherein at least one of the electrode structures of the array of electrode structures has a non-random nanopattern on the sensing surface which provides a different sensing surface area than at least one other electrode structure in the array of electrode structures.

In another aspect of the present application, a calibration method is provided. In one embodiment of the present application, the calibration method may include providing an array of electrode structures each having a sensing surface, wherein at least one of the electrode structures of the array of electrode structures has a non-random nanopattern on the sensing surface which provides a different sensing surface area than at least one other electrode structure in the array of electrode structures. Next, a signal generated by each electrode structure of the array of electrode structures in the presence of an analyte is observed. Each signal is then compared and thereafter the analyte concentration is computed utilizing the comparison of signal data obtained from the sensing surface area of each of the electrode structures.

DETAILED DESCRIPTION

Figure 1A:
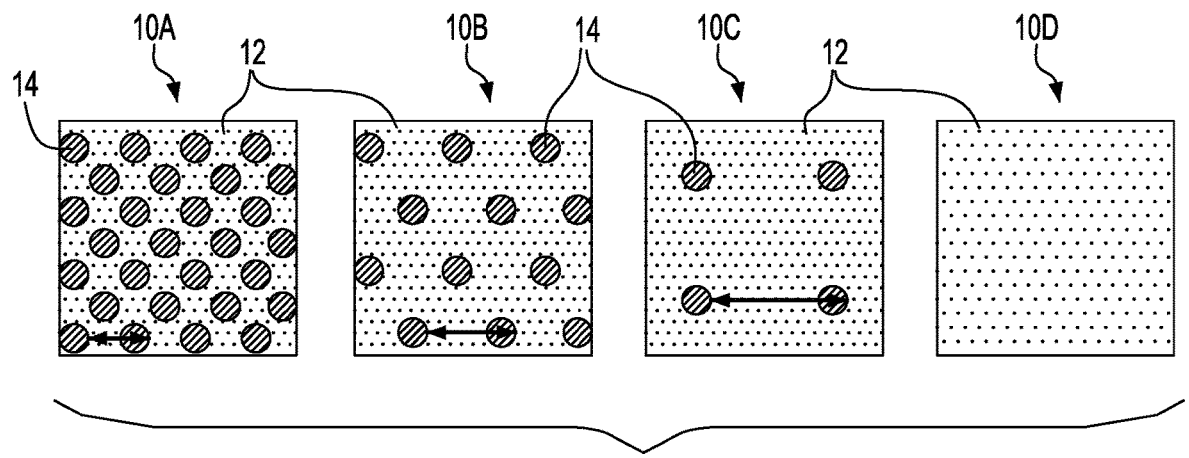
FIG. 1A is a top-down view of a first exemplary biosensor calibration structure that can be employed in the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "beneath" or "under" another element, it can be directly beneath or under the other element, or intervening elements may be present. In contrast, when an element is referred to as being "directly beneath" or "directly under" another element, there are no intervening elements present.

The present application provides biosensor calibration structures which include an array of electrode structures each having a sensing surface, wherein at least one of the electrode structures of the array of electrode structures has a non-random nanopattern on the sensing surface which provides a different sensing surface area than at least one other electrode structure in the array of electrode structures. A nanopattern consists of a series of repeating feature elements with a critical feature size of less than one micron in dimension. The electrode structures of the array of electrode structures that have the non-random nanopattern provide a controlled variation in the surface area which is active for sensing. The known difference in sensing surface area may be translated to a known difference in senor signal. Since the sensor surface area should remain constant and not vary with time or usage throughout the lifetime of the sensor, the difference in signal between electrodes with known surface area variations should also remain constant throughout the sensor. If the signal difference between the electrodes with known surface area does not remain constant, the resulting variation in signal difference can be used to identify an issue with the sensor function or calibration. A real-time calculation can be completed to identify the delta in signal difference between the electrodes, and mathematical adjustment may be completed to compensate for the observed delta in signal difference. Therefore quantifying deviations from the known signal difference between the electrodes can be employed as a sensor calibration mechanism.

Figure 1B:
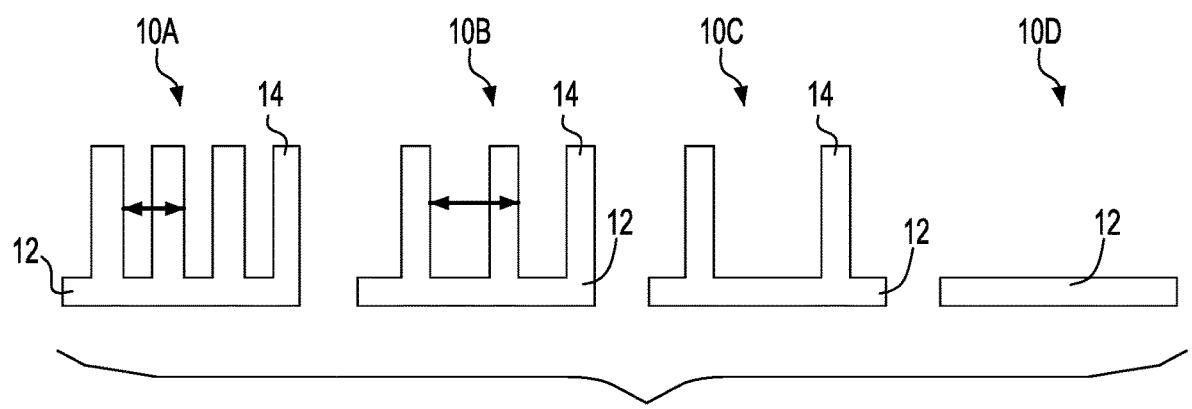
FIG. 1B is a cross-sectional view illustrating one of the rows of the first exemplary biosensor calibration structure shown in FIG. 1A.

Referring first to FIGS. 1A-1B, there are shown a first exemplary biosensor calibration structure that can be employed in one embodiment of the present application. The first exemplary structure shown in FIGS. 1A-1B includes an array of electrode structures 10A, 10B, 10C and 10D. The array of electrode structures shown in FIGS. 1A-1B is typically formed upon a substrate (not shown). The substrate is composed of any material. In one example, the substrate is composed of a material that is compatible for inserting into the human body. Although the present application describes and illustrates four electrode structures within the array of electrode structures, the present application is not limited to that number of electrode structures. Instead, the present application can be used with any number of electrode structures provided that at least one of the electrode structures of the array of electrode structures has a non-random nanopattern on the sensing surface which provides a different sensing surface area than at least one other electrode structure in the array of electrode structures. Thus, the minimum number of electrode structures within the array of electrode structures is two. In this embodiment of the present application, the density/pitch of the non-random nanopattern of each individual electrode structure in the array of electrode structures is altered to provide different sensing surface area. The term "sensing surface area" is used throughout the present application to denote the surfaces of the electrode structure which are exposed to the substance or solution containing the substance to be sensed.

In the embodiment illustrated in FIGS. 1A-1B and by way of one example, the density of the non-random nanopattern feature elements of the electrode structure within the array of electrode structures decreases from left to right. Conversely, and in the embodiment illustrated in FIGS. 1A-1B, the pitch, P (denoted by the double-headed arrow), between each neighboring non-random nanopattern of the electrode structures within the array of electrode structures increases from left to right. Pitch is defined as the minimum distance between repeatable elements which comprise the nanopattern.

In the example shown for the first exemplary biosensor calibration structure, electrode structures 10A, 10B and 10C have a non-random nanopattern located on a sensing surface, while electrode structure 10D does not have any non-random nanopattern located on a sensing surface (thus the electrode structure 10D is flat). Each of the electrode structures (i.e., electrode structure 10A, 10B and 10C) that has a non-random nanopattern located on a sensing surface comprises an electrode base structure 12 having non-random topography (defined by the non-random, i.e., regular repeating, individual features 14). The electrode structure 10D merely includes an electrode base structure 12. In an ideal embodiment, the nanopatterns depicted in 10A, 10B, and 10C would be comprised of features with a constant height, feature cross section, and material composition. Therefore, electrode structure 10A has a greater surface area for active sensing compared to electrode structure 10B, with electrode structure 10B having a greater sensing surface area compared to electrode structure 10C, and electrode structure 10C with a greater sensing surface area compared to electrode structure 10D.

Figure 2A:
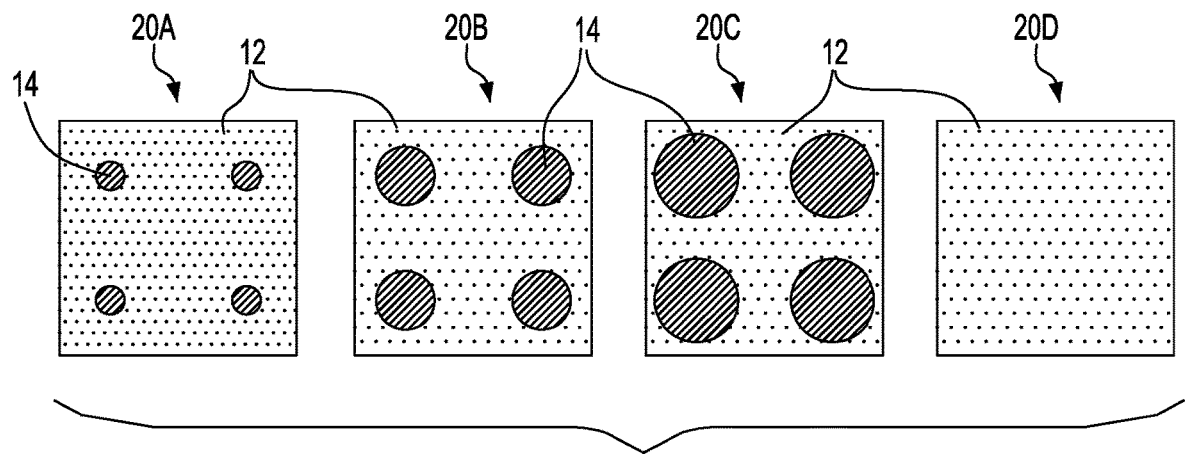
FIG. 2A is a top-down view of a second exemplary biosensor calibration structure that can be employed in the present application.
Figure 2B:
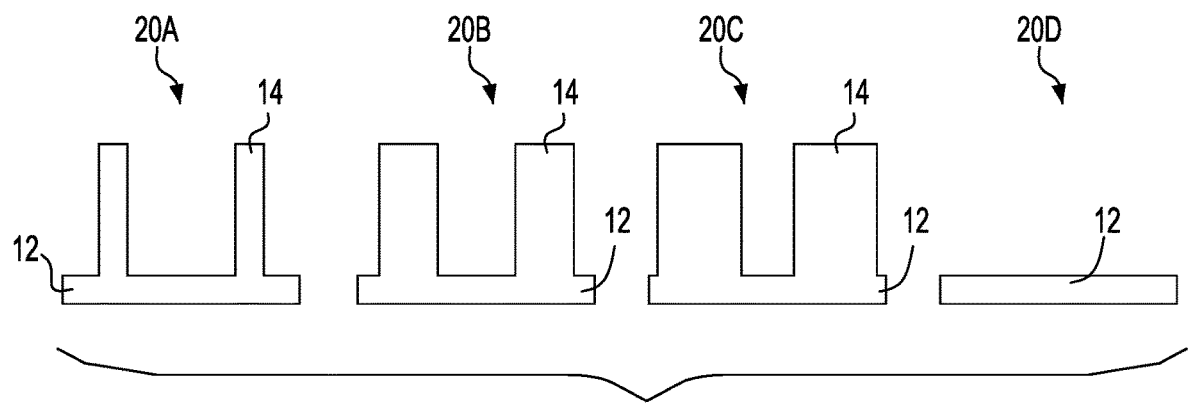
FIG. 2B is a cross-sectional view illustrating one of the rows of the first exemplary biosensor calibration structure shown in FIG. 2A.

Referring now to FIGS. 2A-2B, there are illustrated a second exemplary biosensor calibration structure that can be employed in one embodiment of the present application. The array of electrode structures shown in FIGS. 2A-2B is typically formed upon a substrate (not shown). The substrate is composed of any material. In one example, the substrate is composed of a material that is compatible for inserting into the human body. The second exemplary structure shown in FIGS. 2A-2B also includes an array of electrode structures 20A, 20B, 20C and 20D. Although the present application describes and illustrates four electrode structures within the array of electrode structures, the present application is not limited to that number of electrode structures. Instead, and as mentioned above, the present application can be used with any number of electrode structures provided that at least one of the electrode structures of the array of electrode structures has a non-random nanopattern on the sensing surface which provides a different sensing surface area than at least one other electrode structure in the array of electrode structures.

In this embodiment of the present application, the cross section size or diameter of the non-random nanopattern feature element of each individual electrode structure in the array of electrode structures is altered to provide different sensing surface area. In the embodiment illustrated in FIGS. 2A-2B and by way of one example, the cross section size/diameter of the non-random nanopatterns of the electrode structure within the array of electrode structures increases from left to right.

In the example shown for the second exemplary biosensor calibration structure, electrode structures 20A, 20B and 20C have a non-random nanopattern located on a sensing surface, while electrode structure 20D does not have any non-random nanopattern located on a sensing surface (thus the electrode structure 20D is flat). Each of the electrode structures (i.e., electrode structure 20A, 20B and 20C) that has a non-random nanopattern located on a sensing surface comprises an electrode base structure 12 having non-random topography (defined by the non-random, i.e., regular repeating, individual features 14). The electrode structure 20D merely includes an electrode base structure 12. In an ideal embodiment, the nanopatterns depicted in 20A, 20B, and 20C would be comprised of features with a constant height, pitch, and material composition. Therefore, electrode structure 20C has a greater surface area for active sensing compared to electrode structure 20B, with electrode structure 20B having a greater sensing surface area compared to electrode structure 20A, and electrode structure 20A with a greater sensing surface area compared to electrode structure 20D.

Figure 3:
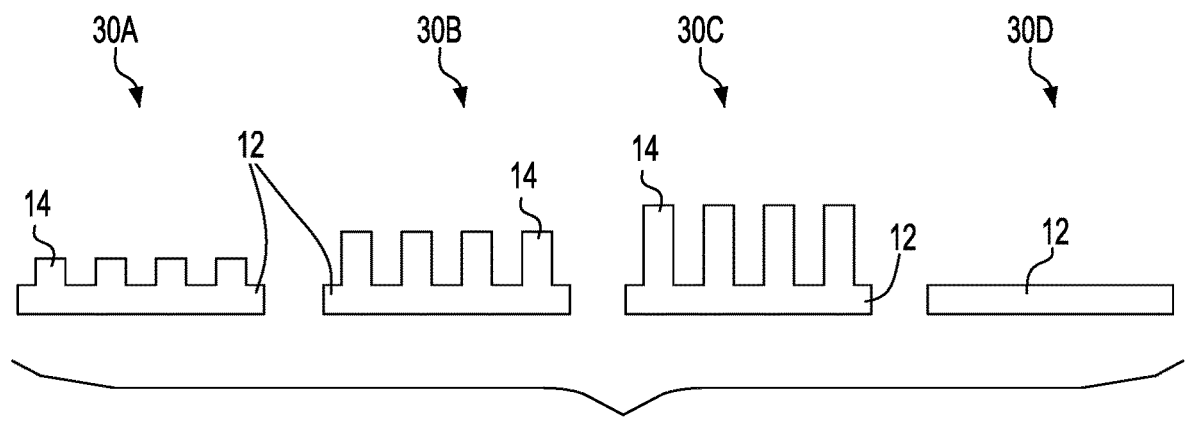
FIG. 3 is a cross sectional view of a third exemplary biosensor calibration structure that can be employed in the present application.

Referring now to FIG. 3, there is illustrated a third exemplary biosensor calibration structure that can be employed in one embodiment of the present application. The array of electrode structures shown in FIG. 3 is typically formed upon a substrate (not shown). The substrate is composed of any material. In one example, the substrate is composed of a material that is compatible for inserting into the human body. The third exemplary structure shown in FIG. 3 also includes an array of electrode structures 30A, 30B, 30C and 30D. Although the present application describes and illustrates four electrode structures within the array of electrode structures, the present application is not limited to that number of electrode structures. Instead, the present application can be used with any number of electrode structures provided that at least one of the electrode structures of the array of electrode structures has a non-random nanopattern on the sensing surface which provides a different sensing surface area than at least one other electrode structure in the array of electrode structures.

In this embodiment of the present application, the height or aspect ratio of the non-random nanopattern feature element of each individual electrode structure in the array of electrode structures is altered to provide different sensing area. In the embodiment illustrated in FIG. 3 and by way of one example, the height or aspect ratio (i.e., ratio of width to height) of the non-random nanopatterns of the electrode structures 30A, 30B and 30C increases from left to right.

In the example shown for the third exemplary biosensor calibration structure, electrode structures 30A, 30B and 30C have a non-random nanopattern located on a sensing surface, while electrode structure 30D does not any have non-random nanopattern located on a sensing surface (thus the electrode structure 30D is flat). Each of the electrode structures (i.e., electrode structure 30A, 30B and 30C) that has a non-random nanopattern located on a sensing surface comprises an electrode base structure 12 having non-random topography (defined by the non-random, i.e., regular repeating, individual features 14). The electrode structure 30D merely includes an electrode base structure 12. In an ideal embodiment, the nanopatterns depicted in 30A, 30B, and 30C would be comprised of features with a constant feature cross section, pitch, and material composition. Therefore, electrode structure 30C has a greater surface area for active sensing compared to electrode structure 30B, with electrode structure 30B having a greater sensing surface area compared to electrode structure 30A, and electrode structure 30A with a greater sensing surface area compared to electrode structure 30D.

In some embodiments and for the electrode structures that have a non-random nanopattern of FIGS. 1A, 1B, 2A, 2B and 3, the electrode base structure 12 and the non-random topography (i.e., the non-random individual articulated features 14) are of uniform construction (i.e., single piece) and uniform composition. That is, such electrode structures lack an interface between the electrode base structure 12 and the non-random individual articulated features 14 that collectively define the non-random topography of the electrode structure. In an alternate embodiment, the electrode structures may be formed of the same composition in a construction which features an interface between the non-random individual articulated features 14 and the electrode base structure 12. In yet another embodiment, the individual articulated features 14 and the electrode base structure 12 may be comprised of different materials which may result in an interface between the electrode base structure 12 and the non-random individual articulated features 14.

The shape of the electrode base structure 12 is not limited to any specific shape. In one embodiment of the present application, the shape of the electrode base structure 12 is a polygonal. In such an embodiment, the shape of the electrode base structure 12 may be triangular, quadrilateral or pentagonal. In other embodiments, the shape of the electrode base structure 12 may be circular or elliptical. The shape of the electrode base structure 12 may also include additional structures such as wiring or probe pads required to read out the electrical signal from each individual electrode structure.

Each non-random individual articulated feature 14 that provides the non-random topography and the non-random nanopattern of the electrode structure has a size that is less than the size of the electrode base structure 12. Each non-random individual articulated feature 14 may have various shapes and sizes. For example, each non-random individual articulated feature 14 may have a shape of a rod, a cone, an ellipse, or an annular structure. In one embodiment of the present application, each non-random individual articulated feature 14 may have a critical dimension ranging in size from 5 nm to 900 nm. In another embodiment of the present application, each non-random individual articulated feature 14 may have a critical dimension ranging in size from 20 nm to 300 nm. In one embodiment of the present application, each non-random individual articulated feature 14 has a pitch ratio of from 2:1 to 100:1. In another embodiment of the present application, each non-random individual articulated feature 14 has a pitch ratio of from 2:1 to 20:1.

In one embodiment of the present application, each non-random individual articulated feature 14 has a height from 5 nm to 300 μm. In another embodiment of the present application, each non-random individual articulated feature 14 has a height from 50 nm to 20 μm. In one embodiment of the present application, each non-random individual articulated feature 14 has an aspect ratio (i.e., ratio of width to height) of 1:1 to 500:1. In another embodiment of the present application, each non-random individual articulated feature 14 has an aspect ratio (i.e., width to height) of 2:1 to 100:1.

Each electrode structure of the array of electrode structures of the present application including the electrode base structure 12 and, when present, each non-random individual articulated feature 14 that provides the non-random topography of at least one of the electrode structures within an array of electrode structures is composed of an electrically conductive material (hereinafter just "conductive material"). In one embodiment of the present application, the electrically conductive material is a metallic glass. By "metallic glass" it is meant a solid metallic material, usually an alloy, with a disordered amorphous atomic structure. Metallic glasses can also be referred to herein as amorphous metals or glassy metals. In the case where the conductive material is a metallic glass, the conductive material can be non-crystalline or amorphous. In some embodiments, the metallic glass that can be used as the conductive material may include an element selected from platinum, copper, nickel, phosphorous, palladium, zirconium, silver, aluminum, carbon or alloy or alloys thereof. In one example, the electrode structure of the present application may be composed of a platinum-based bulk metallic glass alloy such as, but not limited to, a PtCuNiP alloy.

In some embodiments, the conductive material that provides the electrode structures is a conductive metal-containing material including, but not limited to, platinum, copper, silver, gold, tungsten, aluminum, iron, palladium, nickel, titanium, or zirconium. Alloys of these metals may also be employed as the conductive metal-containing material that can provide electrode structures of the array of electrode structures.

The electrode structures can be formed utilizing various techniques. In one embodiment of the present application, electrode structures having the non-random nanopatterns may be formed by first providing a mold having a pattern that comprises both an electrode base structure shape and a nanotopography shape. By "nanotopography shape" is meant an array of non-random (i.e., regular repeating) individual articulated features whose size is less than the size of the electrode base structure shape of the mold. The mold may be composed of any material including for example, a semiconductor material and/or a dielectric material. The mold may be formed by lithography and etching. A conductive material is then formed into the mold. In some embodiments, a metallic seed layer may be formed into the mold prior to forming the conductive material In one embodiment, an amorphous metal, which may also be referred to as a "metallic glass" or a "bulk metallic glass," is introduced into the mold by utilizing a thermoplastic forming process to provide an electrode structure comprising the amorphous metal (i.e., metallic glass) and having the electrode base structure shape and the nanotopography shape resulting from the influence of the mold. In another embodiment, the conductive material that provides the mold may include a conductive metal-containing material as defined above that is electrodeposited on a surface of a metallic seed layer that is provided on the mold. After forming at least the conductive material into the mold and removing any excess conductive material formed outside of the mold, the mold is then removed from the resultant electrode structure utilizing means well known to those skilled in the art.

In another embodiment, electrode structures having the non-random nanopatterns can be formed by first providing an electrode structure comprising a conductive material. Thereafter, lithography and etching can be used to provide the electrode structures with non-random topography.

In yet another embodiment, electrode structures having the non-random nanopatterns can be formed by providing an electrode base structure having an electrode base structure shape on a substrate. Next, a patterned material layer is formed surrounding the electrode base, wherein the patterned material layer contains openings for defining a nanotopography shape of the electrode structure. A metallic seed layer can then be formed on exposed surfaces of the electrode base structure and within the openings of the patterned material layer, and thereafter a conductive metal-containing material is electroplated on the metallic seed layer and within the openings of the patterned material layer to provide the electrode structure comprising the electrode base structure having the electrode base structure shape and the conductive metal-containing material having the nanotopography shape.

In further embodiment, electrode structures having the non-random nanopatterns can be formed by an electrode base structure material on a substrate. Next, a patterned material layer is formed surrounding the electrode base structure material, wherein the patterned material layer contains openings. The electrode base structure material exposed surface is then etched utilizing the patterned material layer as an etch-resistant mask to provide the electrode structure comprising a remaining portion of the electrode base structure material and having an electrode base structure shape and a nanotopography shape. The patterned material layer is then removed.

Details concerning any of the above mentioned fabrication process can be found, for example, in U.S. Ser. No. 15/005,690, filed Jan. 25, 2016, U.S. Ser. No. 15/218,550, filed Jul. 25, 2016 and U.S. Ser. No. 15/419,524, filed Jan. 20, 2017, the entire contents of each are incorporated herein by reference. Electrode structures having a flat surface can be formed utilizing any well known technique.

Figure 4:
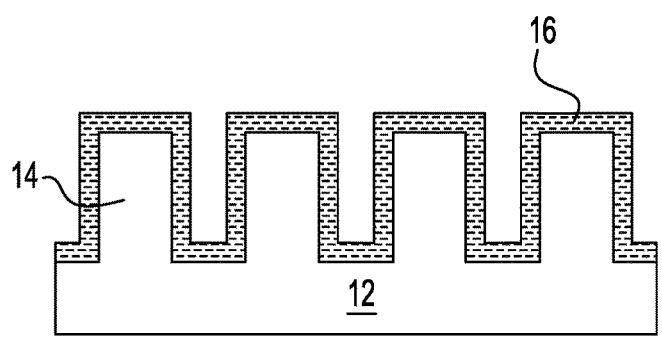
FIG. 4 is cross sectional view illustrating one of the electrode structures of one of the biosensor calibration structures of the present application after providing a biological functionalization material on at least the sensing surface of the electrode structure.

After forming the array of electrode structures and, in order to functionalize the structure to respond as a biosensor, a biological functionalization material can be applied to the surface of the electrode structures including each non-random individual articulated feature 14 that provides the nanotopography shape; for electrode structures that are flat, the biological functionalization material can be formed directly onto a physically exposed flat surface. Any of the exposed areas of the electrode base structure 12 may also be coated with the biological functionalization material. FIG. 4 represents one electrode structure shown in cross section having a non-random nanopattern that can be present in one of the biosensor calibration structures of the present application after providing biological functionalization material 16 on at least the sensing surface of each electrode structure of the array of electrode structures.

By "biological functionalization material" it is meant any bioreceptor that binds with a complementary target biomolecule to create a binding event. In some embodiments, biochemical reactions involving the biological functionalization material generate an electrical signal which can be conducted by the non-random individual articulated features 14 of the electrode structures under an applied electric potential. Examples of biological functionalization materials that can be used in the present application include an oligonucleotide, a nucleic acid, a peptide, a ligand, a protein, an enzyme, or any other material apt to bind with a complementary target biomolecule. When the electrode structures within the array of electrode structures are used for glucose sensing, the biological functionalization material can be composed of glucose oxidase or glucose dehydrogenase.

The biological functionalization material can be applied to the electrode structures utilizing established biological functionalization processes known to those skilled in the art. Such biological functionalization processes typically include a series of chemical reactions that attach the biological functionalization material on the surface of the electrode structure.

The array of electrode structures can be used as a component in various biosensors which include other well-known components, such as but not limited to, reference and counter electrode structures.

The calibration electrode structures of the present application can be used in a calibration method to improve sensor signal and signal sensitivity as well as the accuracy of the signal. The calibration method may include providing an array of electrode structures each having a sensing surface, wherein at least one of the electrode structures of the array of electrode structures has a non-random nanopattern on the sensing surface which provides a different sensing surface area than at least one other electrode structure in the array of electrode structures. In some embodiments, a biological functionalization material, as defined above may be applied to the sensing surface of each electrode structure within the array of electrode structures. Next, a signal generated by each electrode structure of the array of electrode structures in the presence of an analyte is observed. In some embodiments, the analyte is present in a human body. Each signal is then compared and thereafter the analyte concentration is computed utilizing the comparison of signal dated obtain from each electrode structure of the area of electrode structures. If the signal difference between the electrodes with known surface area does not remain constant, the resulting variation in the signal difference can be used to identify an issue with the sensor function or calibration. A real-time calculation can be completed to identify the delta in signal difference between the electrodes, and mathematical adjustment may be completed to compensate for the observed delta in signal difference. The comparison and analyte concentration calculation can be performed by hand or utilizing a computer system.

The term "analyte" is used to refer to a substance or chemical constituent such as a biological fluid (for example, blood, interstitial fluid, cerebral spinal fluid, lymph fluid, or urine) that can be analyzed. Analytes can include naturally occurring substances, artificial substances, metabolites, and/or reaction products. In some embodiments, the analyte for measurement by the sensing areas is glucose. However, other analytes are contemplates as well, including, but not limited to lactate, salts, sugars, proteins, fats, vitamins, and hormones naturally occurring in the blood or interstitial fluids can constitute analytes in certain embodiments. The analyst can be naturally present in biological fluid or endogenous; for example, a metabolic product, a hormone, and antigen, and an antibody. Alternatively, the analyte can be introduced into the body or exogeneous, for example, a contrast agent for imaging, a radioisotope, a chemical agent, a ceutical composition including, but not limited to insulin. The metabolic for drugs and pharmaceutical compositions are also contemplated as analytes.

In some embodiments, a computer or processing system may be used in the calibration method in one embodiment of the present disclosure. Notably, the computer system may be used to run the calibration method and/or providing various other functions such as calculations, comparisons, etc. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The biosensor calibration structure of the present application can be operatively coupled to a variety of other systems elements typically used with analyte sensors (e.g., structural elements such as piercing members, insertion sets and the like as well as electronic components such as processors, monitors, medication infusion pumps and the like), for example to adapt them for use in various contexts (e.g., implantation within a mammal). One embodiment includes monitoring a physiological characteristic of a user using the biosensor calibration structure of the present application. In typical embodiments, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments include devices which display data from measurements of a sensed physiological characteristic (e.g., blood glucose concentrations) in a manner and format tailored to allow a user of the device to easily monitor and, if necessary, modulate the physiological status of that characteristic (e.g., modulation of blood glucose concentrations via insulin administration). An illustrative embodiment is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g., text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device.

An illustrative system embodiment consists of a glucose sensor, a transmitter and pump receiver and a glucose meter. In this system, radio signals from the transmitter can be sent to the pump receiver periodically (e.g., every 5 minutes) to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection.

Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g., an insulin pump). Typically in such devices, the physiological characteristic values include a plurality of measurements of blood glucose.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A biosensor calibration structure comprising:
an array of electrode structures each having a sensing surface, wherein at least one of the electrode structures of the array of electrode structures has a non-random nanopattern comprising an electrode base structure having a topography and in a first sensing surface which provides a different sensing surface area than at least one other electrode structure in the array of electrode structures, wherein the at least one other electrode structure of the array of electrode structures is an entirely non-patterned sensing surface located outside of the first sensing surface.

2. The biosensor calibration structure of claim 1, wherein each electrode structure of the array of electrode structures comprises an electrically conductive material.

3. The biosensor calibration structure of claim 1, wherein the electrode base structure and the topography are of uniform construction and comprise a same electrically conductive material.

4. The biosensor calibration structure of claim 1, wherein the topography comprises rods, cones, or annular structures.

5. The biosensor calibration structure of claim 1, further comprising a biological functionalization material located on at least the sensing surface of each electrode structure of the array of electrode structures.

6. The biosensor calibration structure of claim 5, wherein the biological functionalization material is composed of an oligonucleotide, a nucleic acid, a peptide, a ligand, a protein, an enzyme, or any other material apt to bind with a complementary target biomolecule.

7. The biosensor calibration structure of claim 6, wherein the biological functionalization material is composed of glucose oxidase or glucose dehydrogenase.

8. The biosensor calibration structure of claim 1, wherein the non-random nanopattern consists of repeating feature elements having a critical feature size of less than one micron in dimension.

9. A biosensor calibration structure comprising:
an array of electrode structures each having a sensing surface, wherein at least one of the electrode structures of the array of electrode structures has a non-random nanopattern comprising an electrode base structure having a first topography and in a first sensing surface which provides a different sensing surface area than at least one other electrode structure in the array of electrode structures, wherein the at least one other electrode structure of the array of electrode structures has another non-random nanopattern comprising the electrode base structure having the first topography in a second sensing surface, and the at least one other electrode structure of the array of electrode structures has one of the following: (i) a different density than the non-random nanopattern of the at least one of the electrode structures of the array of electrode structures (ii) a different cross sectional size than the non-random nanopattern of the at least one of the electrode structures of the array of electrode structures, or (iii) a different aspect ratio than the non-random nanopattern of the at least one of the electrode structures of the array of electrode structures.

10. The biosensor calibration structure of claim 9, further comprising a biological functionalization material located on at least the sensing surface of each electrode structure of the array of electrode structures.

* * * * *